(12) United States Patent
Ogawa

(10) Patent No.: US 6,350,874 B1
(45) Date of Patent: Feb. 26, 2002

(54) METHOD FOR PRODUCING TRIETHYLENEDIAMINES AND PIPERAZINES

(75) Inventor: Tsukasa Ogawa, Kanagawa (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/536,454

(22) Filed: Mar. 28, 2000

(30) Foreign Application Priority Data

Apr. 1, 1999 (JP) .......................... 11-094828

(51) Int. Cl.$^7$ .......................... C07D 295/023
(52) U.S. Cl. .......................... 544/352; 544/358
(58) Field of Search .................. 544/352, 358

(56) References Cited

U.S. PATENT DOCUMENTS

| | | | |
|---|---|---|---|
| 3,956,329 A | * 5/1976 | Murakami et al. | 260/268 |
| 5,041,548 A | 8/1991 | Sato et al. | 544/352 |
| 5,756,741 A | 5/1998 | Armor et al. | 544/352 |
| 6,084,096 A | * 7/2000 | Li et al. | 544/352 |

FOREIGN PATENT DOCUMENTS

| | | |
|---|---|---|
| EP | 0382055 A1 | 8/1990 |
| EP | 0423526 A2 | 4/1991 |
| EP | 0831096 A2 | 3/1998 |

OTHER PUBLICATIONS

Kirk–Othmer Encyclopedia of Chemical Technology 3$^{rd}$ Ed. vol. 7 pp. 585–587 Copper Alloys to Distillation.

* cited by examiner

*Primary Examiner*—Richard L. Raymond
*Assistant Examiner*—Thomas C McKenzie
(74) *Attorney, Agent, or Firm*—Nixon & Vanderhye

(57) ABSTRACT

A method for producing triethylenediamines and piperazines, which comprises contacting an amine compound having a group of the formula (1):

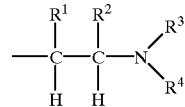

(1)

wherein each of $R^1$ to $R^4$ which are independent of one another, is a hydrogen atom or a $C_{1-3}$ alkyl group which may have a substituent, with a catalyst consisting of a crystalline aluminosilicate calcinated at a temperature of from 500 to 950° C. and then contacted with an inorganic acid, and having a molar ratio of silica to alumina of at least 12.

5 Claims, No Drawings

METHOD FOR PRODUCING TRIETHYLENEDIAMINES AND PIPERAZINES

BACKGROUND OF THE INVENTION

1. Field of the Invention

The present invention relates to a method for producing triethylenediamines and piperazines. Particularly, it relates to a method for effectively and efficiently producing triethylenediamines and piperazines from an amine compound by using an improved crystalline aluminosilicate catalyst.

2. Discussion of Background

Triethylenediamines are useful compounds which are widely used as e.g. a foaming catalyst or an epoxy resin curing accelerator in production of a polyurethane, and piperazines are useful compounds which are widely used as e.g. intermediates for syntheses of pharmaceuticals and agricultural chemicals, or an urethane catalyst.

Such triethylenediamines and piperazines can be obtained usually by cyclization of an amine compound by using a catalyst.

As the catalyst, zeolites have been known. For example, JP-A-50-58096 discloses a method for obtaining triethylenediamine and piperazine by using an A-type zeolite as the catalyst and contacting N-(2-aminoethyl)piperazine with said catalyst at a temperature of from 250 to 450° C. in a gas phase. JP-A-60-260574 discloses a method for obtaining triethylenediamine by using a high silica zeolite of a composition having a molar ratio of silica to alumina of at least 20, as the catalyst, and contacting N-(2-aminoethyl)piperazine or N-(2-hydroxyethyl)piperazine with said catalyst at a temperature of from 250 to 550° C. in a gas phase. JP-A-62-228079 discloses a method for obtaining triethylenediamine by using, as the catalyst, a crystalline metal silicate having a molar ratio of silica to alumina of at least 12 and having a calcination treatment applied thereto in the air atmosphere at a temperature of from 400 to 600° C., and contacting e.g. monoethanolamine, ethylenediamine, N-(2-aminoethyl)piperazine or N-(2-hydroxyethyl)piperazine with said catalyst at a temperature of from 100 to 500° C. JP-A-63-122654 discloses a method for obtaining triethylenediamine by using, as the catalyst, a crystalline metal silicate having a molar ratio of silica to alumina of at least 12 and having a calcination treatment applied thereto in the air atmosphere at a temperature of from 400 to 600° C., and contacting e.g. monoethanolamine, ethylenediamine, piperazine, N-(2-aminoethyl)piperazine or N-(2-hydroxyethyl)piperazine with said catalyst at a temperature of from 100 to 500° C. under an absolute pressure of at least 30 kPa(3 kg/cm$^2$). JP-A-1-132587 discloses a method for obtaining triethylenediamine by using a pentasyl-type zeolite as the catalyst, and contacting piperazine with said catalyst at a temperature of from 250 to 550° C. JP-A-1-143864 discloses a method for obtaining triethylenediamine by using a pentasyl-type zeolite as the catalyst, and contacting ethylenediamine, diethylenetriamine or 2-aminoethanol with said catalyst at a temperature of from 250 to 550° C. JP-A-3-127764 discloses a method for obtaining triethylenediamine by using at least one molecular sieve selected from the group consisting of silica molecular sieves, non-zeolite type molecular sieves and zeolite type molecular sieves, as the catalyst, and contacting e.g. N-(2-aminoethyl)piperazine, N-(2-hydroxyethyl)piperazine, piperazine, piperazine and monoethanolamine, or piperazine and ethylenediamine, with said catalyst at a temperature of from 250 to 500° C. JP-A-3-133971 discloses a method for obtaining triethylenediamine by using a pentasyl type zeolite containing an alkali metal or having aluminum in the zeolite framework isomorphically substituted by iron, as the catalyst, and contacting ethylenediamine with said catalyst at a temperature of from 270 to 420° C. Further, JP-A-5-17460 discloses a method for producing triethylenediamine from an amine compound and a catalyst consisting of a crystalline aluminosilicate having calcination treatment applied thereto at a temperature of from 500 to 950° C. in a water vapor atmosphere. JP-A-5-17461 discloses a method for producing triethylenediamine from an amine compound and a catalyst consisting of a crystalline aluminosilicate having calcination treatment applied thereto at a temperature of from 610 to 950° C. in the air atmosphere. JP-A-5-17462 discloses a method for producing triethylenediamine from an amine compound and a crystalline aluminosilicate catalyst having an inorganic salt supported thereon. JP-A-10-109964 discloses a method for producing triethylenediamine from an amine compound and a zeolite catalyst having basic treatment applied thereto. JP-A-10-182562 discloses a method for producing triethylenediamine from an amine compound and a surface acidity-deactivated zeolite catalyst. Further, JP-A-10-195029 discloses a method for producing triethylenediamine from a triethylenediamine reaction solution having an ethylated compound added thereto and a condensation/cyclization selective zeolite.

As mentioned above, many methods for producing triethylenediamine by using a zeolite catalyst have been disclosed. However, there are following problems in the case where the zeolite catalyst is used industrially.

Namely, in the method as disclosed in JP-A-50-58096, the selectivities of triethylenediamine and piperazine are low, whereby the yields cannot be kept high, and the decrease in activity of said catalyst with time is significant, whereby the catalyst can not be used industrially. In the method as disclosed in JP-A-60-260574, although the selectivities of triethylenediamine and piperazine are high, the conversion is low, whereby the yield can not be kept high, and further, the decrease in activity of said catalyst with time is significant, whereby it is not economically advantageous to use said catalyst as an industrial catalyst. In the methods as disclosed in JP-A-62-228079 and JP-A-63-122654, although the selectivity can be increased when the conversion is low, the selectivity will decrease when the conversion is increased, whereby the desired compound can not be obtained with a high yield, and similarly, the decrease in activity of said catalyst with time is significant, and accordingly, said catalyst can hardly be used as an industrial catalyst. In the methods as disclosed in JP-A-1-132587 and JP-A-1-143864, although the selectivity is high, the conversion is low at that time and the yield of the desired compound is thereby low, and similarly, the decrease in activity of said catalyst with time is significant. In the method as disclosed in JP-A-3-127764, although the selectivity of triethylenediamine is high, the conversion is low, whereby the yield of triethylenediamine can not be kept high, and similarly, the decrease in activity of said catalyst with time is significant. In the method as disclosed in JP-A-3-133971, in the case of the alkali metal ion-containing pentasyl zeolite, although the selectivity is high, the conversion is low, and the yield of the desired compound is thereby low, and in the case of the pentasyl zeolite having aluminum in the zeolite framework substituted by iron, although the conversion is improved and the selectivity is high, and the yield is thereby improved, but the catalyst is a special zeolite, its production method is complicated and the condition therefore is severe, and its production is costly, and such is not advantageous economically. Further, although the decrease in activity with time is reduced as compared with a conventional catalyst, the decrease is not at an industrially tolerable level. In the methods as described in JP-A-5-17460, JP-A-5-17461 and JP-A-5-17462, although the yield of triethylenediamine is improved, the decrease in activity of the catalyst with time is significant. In the methods as disclosed in JP-A-10-109964 and JP-A-10-182562, the yield of triethylenediamine is low, and the decrease in activity of the catalyst with time is significant, and accordingly, the method can scarcely be used industrially. Further, the method as disclosed in JP-A-10-195029 comprises two-step reaction, whereby the operation is complicated and the equipment cost is high, and further, the decrease in activity of the catalyst is significant.

Namely, in most of the conventional production methods, the yields of the triethylenediamine and the piperazine are low, and they are nonproductive and uneconomical. Further, in the methods which increase these yields, the operation is complicated, the equipment is complex, or a special catalyst which is difficult to industrially produce is used, and such methods are not economical.

Further, as a vital problem, the decrease in catalytic activity with time is significant in any of the conventional catalysts. Namely, the catalyst life is short, which raises the cost for catalyst, and besides, makes the running operation complicated due to variation in composition of the product and the operation for changing the catalyst, and such is the greatest object to overcome industrially.

As mentioned above, a catalyst to produce triethylenediamines and piperazines with high yields stably for a long time, has not been found yet. Accordingly, it has been strongly desired to develop a catalyst having excellent performances, and to develop a production method employing it.

SUMMARY OF THE INVENTION

The present inventor has conducted extensive studies on a method for producing triethylenediamines and piperazines, and as a result, he has concluded that an important factor is a catalyst, and he has further conducted studies on a catalyst. As a result, he has found that triethylenediamines and piperazines can be produced with high yields stably for a long time, which is an object of the present invention, by subjecting a crystalline aluminosilicate to a heat treatment at a high temperature within a specific range, treating it with a specific chemical, adjusting its molar ratio of silica to alumina to be a specific value, and using it as a catalyst, and the present invention has been accomplished on the basis of these discoveries.

Namely, the present invention provides a method for producing triethylenediamines and piperazines, which comprises contacting an amine compound having a group of the following formula (1):

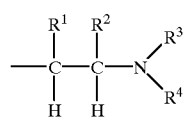

(1)

wherein each of $R^1$ to $R^4$ which are independent of one another, is a hydrogen atom or a $C_{1-3}$ alkyl group which may have a substituent, with a catalyst consisting of a crystalline aluminosilicate calcinated at a temperature of from 500 to 950° C. and then contacted with an inorganic acid, and having a molar ratio of silica to alumina of at least 12.

DETAILED DESCRIPTION OF THE PREFERRED EMBODIMENTS

The crystalline aluminosilicate used as the catalyst in the method of the present invention, is one having a molar ratio of silica to alumina of at least 12, preferably from 40 to 5000. Here, if the molar ratio of silica to alumina is less than 12, the selectivity of the triethylenediamines will decrease, and a large quantity of unnecessary by-product will form. Further, if the molar ratio of silica to alumina is higher than 5000, the catalytic activity will significantly decrease, and the yield will slightly decrease. A catalyst having the molar ratio of from 40 to 5000 is economical and preferred since the catalyst life can be kept long, and besides, the catalytic activity i.e. the yield can be kept high.

The crystalline aluminosilicate used in the method of the present invention, has a molar ratio of silica to alumina of at least 12, and one having a main cavity of oxygen ten-membered ring is preferred since the catalytic activity and the catalyst life can be increased. Its specific examples include ZSM-5 as disclosed in U.S. Pat. No. 3,702,886, ZSM-8 as disclosed in U.S. Pat. No. 1,334,243, ZSM-11 as disclosed in U.S. Pat. No. 3,709,979, ZSM-12 as disclosed in U.S. Pat. No. 3,832,449 and ZSM-21 as disclosed in U.S. Pat. No. 4,001,346.

The crystalline aluminosilicate is obtained usually by hydrothermal synthesis, in which an organic crystallizing agent may be used or may not be used, and either is applicable to the present invention.

In the method of the present invention, said crystalline aluminosilicate is calcinated at a temperature of from 500 to 950° C. The calcination is carried out either on its powder or on its molded product. The molded product is usually obtained by mixing and kneading a crystalline aluminosilicate powder with an inorganic binder such as clay, an alumina sol or a silica sol, an organic binder of cellulose type and a small amount of water, followed by wet granulation. The operation of mixing and kneading is important to impart mechanical strength for the molded product, and the apparatus therefor may, for example, be a rotating container type mixer of e.g. cylindrical type, V type, cubic type, double circular cone type, hexagonal type or pyramid type, or a container-fixed type mixer such as a screw mixer, a ribbon mixer, a Henschel mixer or a rotation pan mixer. The wet granulation is important to arrange the shape to improve operation efficiency and workability, and to increase mechanical strength of the molded product. The method may be extrusion granulation, agitation-mixing granulation or pressure molding, and depending upon the method, the molded product may be in the form of e.g. pellets, beads or tablets, and any of these may be used. After such a wet granulation, drying to remove water is usually carried out. As the inorganic binder for molding, a silica type binder such as a silica sol is preferred, since decrease of catalytic performances, particularly decrease in catalytic activity with time, can be suppressed. The calcination is carried out either in the air atmosphere or in a water vapor atmosphere. The conditions vary depending upon e.g. the type of the crystalline aluminosilicate, the molar ratio of silica to alumina, the type of the organic crystallizing agent and the type of the binder in the case of the molded product. However, the temperature is within a range of from 500 to 950° C., preferably from 550 to 850° C., in any case. The calcination time is usually at least 1 hour, preferably at least 3 hours. If the calcination temperature is less than 500° C., the selectivities of the triethylenediamines and the piperazines which are the desired compounds, will significantly decrease. Further, if the calcination temperature is higher than 950° C., the crystallinity of the crystalline aluminosilicate will decrease due to heat, the specific surface area will decrease, and the activity as a catalyst will significantly decrease. By calcination at a temperature within a range of from 550 to 850° C., a catalyst having more excellent catalytic activity and catalyst life can be obtained.

In the method of the present invention, after the calcination, the crystalline aluminosilicate is contacted with an inorganic acid. Said operation is one of great characteristics of the present invention. The contact treatment is carried out by contacting the calcinated crystalline aluminosilicate usually with an aqueous solution of an inorganic acid, and the operation is carried out by any of batch method (dipping method), column flow method or column circulation method. In the case of the batch method, the operation may be repeated, whereby the effect will increase. However, the column flow method or the column circulation method is preferred from the viewpoint of operation efficiency.

The treatment temperature and the time vary depending upon e.g. the type of the crystalline aluminosilicate to be used, the calcination conditions, the type of the inorganic acid and the concentration of the inorganic acid, and can not absolutely be determined. However, the contact treatment is carried out at a temperature of usually from 20 to 100° C., preferably from 50 to 80° C., for from 1 to 100 hours, preferably from 3 to 50 hours, to obtain an excellent catalyst.

The inorganic acid to be used in the present invention is not particularly limited, and examples of which include hydrogen fluoride, hydrogen chloride, hydrogen bromide, sulfuric acid, nitric acid and perchloric acid. Among these, preferred are hydrogen chloride, sulfuric acid and nitric acid, and particularly preferred is hydrogen chloride, from the viewpoint of treatment effect, availability, price and handling efficiency.

The concentration of the aqueous solution of an inorganic acid to be used is usually from 0.01 to 10 mol/l. If it is less than 0.01 mol/l, a longer time for contact treatment may be required, or a larger amount of the aqueous solution of an inorganic acid may be required, and the effect of the contact treatment will decrease. Further, if it is higher than 10 mol/l, the crystalline aluminosilicate will be deteriorated, its crystallinity will decrease, and its activity as a catalyst will decrease. In the case of an extremely strong acid such as hydrogen fluoride, an aqueous solution having a lower concentration is used so as to suppress dissolution of the crystalline aluminosilicate.

The amount of the aqueous solution of an inorganic acid is not particularly limited. However, if it is too small, the effect of the treatment will be small, and if it is too large, the cost for the inorganic acid will increase, but the effect will no longer improve so much. The solution is used usually in at least the same amount by weight as the crystalline aluminosilicate, preferably in an amount from twice to 20 times by weight.

The waste acid after the use for the contact treatment of the catalyst may be used again when the acid concentration in the waste acid is within the above range, and may be used by further adding an inorganic acid thereto.

After the contact treatment by an inorganic acid, the catalyst is usually washed with water and dried. The drying operation is not particularly required when ion exchange is successively carried out. By the contact with an inorganic acid, a catalyst having high performances, i.e. a catalyst which produces triethylenediamines and piperazines with high yields, and of which the decrease in activity with time can be suppressed (i.e. of which the life is long), can be obtained.

The crystalline aluminosilicate to be used in the present invention is not particularly limited to H type, and may have part or whole of its hydrogen ions exchanged by other cation such as lithium ions, sodium ions, potassium ions, cesium ions, magnesium ions, calcium ions or lanthanum ions. After the contact treatment with an inorganic acid, the crystalline aluminosilicate is H type, and may be exchanged by the above cation, to use as a catalyst. Here, the crystalline aluminosilicate having its hydrogen ions exchanged by alkali metal ions, particularly by sodium ions or potassium ions, is preferred from the viewpoint of high yield and suppress of decrease in activity with time, and the alkali metal ion exchange ratio is most preferably from 30 to 70%.

In the method of the present invention, the form of the catalyst is not particularly limited, and it is used as a powder or as a molded product, depending upon the reaction mode. For example, a powder or a granule is used in a slurry bed, and a molded product in the form of tablets, beads or pellets is used in a fixed bed.

The molded product will be obtained by the above molding operation. The molding operation may be carried out after the contact treatment with an inorganic acid, but it is preferably carried out before the calcination operation, as mentioned above, from the viewpoint of improvement of the catalytic performances and the improvement of the operation efficiency. In the case where the molding operation is carried out after the contact treatment with an inorganic acid, it is preferred to carry out molding under an elevated molding pressure, whereby a molded product having higher strength will be obtained. Further, a binder may be used so as to increase the strength of the molded product.

The material compound to be used in the present invention is not particularly limited so long as it is an amine compound having a group of the above formula (1) in its molecule. The compound may, for example, be monoethanolamine, diethanolamine, isopropanolamine, diisopropanolamine, N-(2-aminoethyl)ethanolamine, N-(2-hydroxyethyl)piperazine, N,N'-bis(2-hydroxyethyl) piperazine, N-(2-aminoethyl)piperazine, N,N'-bis(2-aminoethyl)piperazine, piperazine, ethylenediamine, diethylenetriamine, triethylenetetramine or tetraethylenepentamine, and any of these may be used. Among these, a chain ethyleneamine such as ethylenediamine, diethylenetriamine, triethylenetetramin or tetraethylenepentamine, or a cyclic ethyleneamine such as N-(2-aminoethyl)piperazine or piperazine is preferred, since not only they can be available in a large amount at a low cost, but also the triethylenediamine and the piperazine can be produced with higher yields. The more preferred ethyleneamine is N-(2-aminoethyl)piperazine. Said amine compound may be used alone or in combination as a mixture of at least two of the above amine compounds.

In the method of the present invention, the reaction may be carried out either in a gas phase or in a liquid phase. The reaction may be carried out by any of batch system, semi-batch system or continuous system, and it may be carried out in slurry bed (flow bed in a gas phase reaction) or by fixed bed flow system. Industrially, fixed bed flow system is advantageous from the viewpoint of operation, apparatus and economy.

It is advantageous to carry out the reaction by a gas phase system from the viewpoint of operation, yield and stability of the catalyst. In the gas phase system, the amine compound may be diluted by using, as the diluent for the amine compound, an inert gas such as nitrogen gas, hydrogen gas, ammonia gas, water vapor or a gas of e.g. a hydrocarbon, or an inert solvent such as water or an inert hydrocarbon, and the diluted amine compound may be introduced as the material to carry out the reaction. Such a diluent may be used in an optional amount, and usually the molar ratio of the amine compound to the diluent is preferably from 0.01 to 1. If the molar ratio is smaller than 0.01, productivities of the triethylenediamines and the piperazines tend to be low. Further, if the molar ratio is larger than 1, the selectivities for the triethylenediamine and the piperazine will slightly decrease.

In the present invention, an amine compound is used as the material and contacted with the above catalyst consisting of a crystalline aluminosilicate to produce triethylenediamines and piperazines. The reaction conditions such as the reaction temperature and the space velocity vary depending upon e.g. the types of the crystalline aluminosilicate and the amine compound, and can not absolutely be determined. Usually the reaction is suitably carried out at a reaction temperature of from 250 to 450° C. at a space velocity (GHSV) of from 100 to 10000 $hr^{-1}$.

Further, the reaction may be carried out any of under atmospheric pressure, elevated pressure or reduced pressure.

With respect to the catalyst prepared by the method of the present invention, the activity will gradually decrease by the reaction of an extremely long time, as compared with the conventional catalysts. However, by calcinating organic components attached to the catalyst, the catalyst can be regenerated as a catalyst having a high activity, and can be used repeatedly. This indicates that the catalyst is not essentially deteriorated, which is a great characteristic of the present invention. The calcination temperature to activate the used catalyst is usually preferably at least 500° C.

Now, the present invention will be described in further detail with reference to Examples. However, it should be understood that the present invention is by no means restricted to such specific Examples.

CATALYST PREPARATION EXAMPLE 1

100 Parts by weight of powder ZSM-5 type zeolite (860NHA manufactured by Tosoh Corporation, molar ratio of silica to alumina: 72) was subjected to extrusion molding by using 33 parts by weight of silica as a binder, followed by calcination in a water vapor atmosphere at 750° C. for 4 hours, to obtain H-type ZSM-5 (1).

CATALYST PREPARATION EXAMPLE 2

100 g of the H-type ZSM-5 (1) was packed in a column, and 1 l of 1 mol/l hydrochloric acid was circulated therethough at 60° C. for 24 hours at a rate of 1 l/Hr, followed by washing with water until the pH became neutral. Then, 1 l of a 0.5 mol/l sodium chloride aqueous solution was circulated through the column at 80° C. for 8 hours at a rate of 1 l/Hr to carry out Na exchange, followed by washing with water until chlorine ion become undetectable. Then, the content was drew out from the column and dried at 120° C. for 16 hours to obtain Na-type ZSM-5 (2). The Na exchange ratio was 45%.

CATALYST PREPARATION EXAMPLE 3

The same operation as in Catalyst Preparation Example 2 was carried out except that 0.5 mol/l sulfuric acid was used instead of the 1 mol/l hydrochloric acid, to obtain Na-type ZSM-5 (3).

CATALYST PREPARATION EXAMPLE 4

The same operation as in Catalyst Preparation Example 2 was carried out except that a molded product (1) was used instead of the H-type ZSM-5 (1), to obtain Na-type ZSM-5 (4).

CATALYST PREPARATION EXAMPLE 5

A molded product (1) was calcinated in an air atmosphere at 400° C. for 4 hours, and then the same operation as in Catalyst Preparation Example 2 was carried out, to obtain Na-type ZSM-5 (5).

CATALYST PREPARATION EXAMPLE 6

The Na-type ZSM-5 (4) was calcinated in a water vapor atmosphere at 750° C. for 4 hours, to obtain Na-type ZSM-5 (6).

EXAMPLE 1

The Na-type ZSM-5 (2) obtained in Catalyst Preparation Example 2 was packed in a reaction tube of fixed bed flow type, and a mixture of N-(2-aminoethyl) piperazine (hereinafter referred to simply as N-AEP) and water (molar ratio of N-AEP/water: 5/95) was supplied thereto at a space velocity (GHSV) of 1000 $hr^{-1}$ at a reaction temperature of 350° C. The reaction solution was analyzed by gas chromatography. At the beginning of the reaction, the conversion of N-AEP was 99.5%, the yield of triethylenediamine (hereinafter referred to simply as TEDA) was 50.7 wt %, and the yield of piperazine (hereinafter referred to simply as P) was 20.2 wt %, such being high. Further, 30 days after the initiation of the reaction, at a reaction temperature of 370° C., the conversion of N-AEP was 98.2%, the TEDA yield was 47.7 wt %, and the P yield was 20.8 wt %, and a high activity could be kept for a long time.

EXAMPLE 2

The reaction was carried out in the same manner as in EXAMPLE 1, except that the material was changed into a mixture of triethylenetetramine (hereinafter referred to simply as TETA) and water (molar ratio of TETA/water: 8/92). At the beginning of the reaction, at a reaction temperature of 360° C., the conversion of TETA was 100%, the TEDA yield was 45.2 wt %, and the P yield was 14.8 wt %. In the process of the reaction, the temperature was raised, and 20 days after the initiation of the reaction, at a reaction temperature of 370° C., the conversion of TETA was 100%, the TEDA yield was 43.7 wt %, the P yield was 14.9 wt %, and a high activity could be kept.

EXAMPLE 3

The reaction was carried out in the same manner as in EXAMPLE 1, except that the material was changed into a mixture of N-(2-hydroxyethyl)piperazine (hereinafter referred to simply as HEP) and water (molar ratio of HEP/water: 8/92). At a reaction temperature of 340° C., the conversion of HEP was 98.6%, the TEDA yield was 68.1 wt %, the P yield was 4.1 wt %, and a high reaction activity could be obtained under milder conditions. Further, the high reaction activity could be kept for a long time.

EXAMPLE 4

The same operation as in EXAMPLE 1 was carried out except that the Na-type ZSM-5 (3) was used instead of the Na-type ZSM-5 (2). At the beginning of the reaction, at a reaction temperature of 355° C., the conversion of N-AEP was 99.1%, the TEDA yield was 49.8 wt %, and the P yield was 20.5 wt %. Further, 32 days after the initiation of the reaction, at a reaction temperature of 370° C., the conversion of N-AEP was 97.0%, the TEDA yield was 46.3%, the P yield was 21.0 wt %, and a good reaction result could be obtained as in EXAMPLE 1.

COMPARATIVE EXAMPLE 1

The reaction was carried out in the same manner as in EXAMPLE 1 by using the H-type ZSM-5 (1) as the catalyst. At the beginning of the reaction, at a reaction temperature of 355° C., the conversion of N-AEP was 100%, the TEDA yield was 51.4 wt %, and the P yield was 15.1 wt %. However, 30 days after the initiation of the reaction, at a reaction temperature of 370° C., the conversion of N-AEP was 76.7%, the TEDA yield was 33.6 wt %, the P yield was 17.9 wt %, and the activity suddenly dropped.

COMPARATIVE EXAMPLE 2

The reaction was carried out in the same manner as in EXAMPLE 1 by using the H-type ZSM-5 (4) as the catalyst. At the beginning of the reaction, at a reaction temperature of 380° C, the conversion of N-AEP was 97.9%, the TEDA yield was 24.2 wt %, and the P yield was 28.5 wt %. Further, 10 days after the initiation of the reaction, even at a reaction temperature of 400° C., the conversion of N-AEP was 81.8%, the TEDA yield was 19.7 wt %, the P yield was 30.6 wt %, and the decrease in activity was significant. Further, the pressure loss at the catalyst layer increased with time. This was found to be due to breaking and degradation of the molded product, from studies on the catalyst layer after the test.

COMPARATIVE EXAMPLE 3

The reaction was carried out in the same manner as in EXAMPLE 1 by using the H-type ZSM-5 (5) as the catalyst. At the beginning of the reaction, at a reaction temperature of 365° C., the conversion of N-AEP was 99.3%, the TEDA yield was 38.1 wt %, and the P yield was 16.8 wt %. However, 10 days after the initiation of the reaction, even at a reaction temperature of 380° C., the conversion of N-AEP was 82.1%, the TEDA yield was 32.4 wt %, the P yield was 18.2 wt %, and the activity suddenly decreased.

COMPARATIVE EXAMPLE 4

The reaction was carried out in the same manner as in EXAMPLE 1 by using the H-type ZSM-5 (6) as the catalyst. At the beginning of the reaction, at a reaction temperature of 355° C., the conversion of N-AEP was 99.3%, the TEDA yield was 49.7 wt %, and the P yield was 18.9 wt %. Further, 10 days after the initiation of the reaction, even at a reaction temperature of 380° C., the conversion of N-AEP was 91.9%, the TEDA yield was 39.9 wt %, the P yield was 19.4 wt %, and the activity suddenly decreased.

The results are shown in Table 1.

TABLE 1

|  | Catalyst | Material | Elapsed time | Reaction temperature (° C.) | Conversion (%) | TEDA yield (wt %) | P yield (wt %) |
|---|---|---|---|---|---|---|---|
| Ex. 1 | Na-type ZSM-5 (2) | N-AEP | Beginning | 355 | 99.5 | 50.7 | 20.2 |
|  |  |  | After 30 days | 370 | 98.2 | 47.7 | 20.8 |
| 2 | Na-type ZSM-5 (2) | TETA | Beginning | 360 | 100.0 | 45.2 | 14.8 |
|  |  |  | After 20 days | 370 | 100.0 | 43.7 | 14.9 |
| 3 | Na-type ZSM-5 (2) | HEP | Beginning | 340 | 98.6 | 68.1 | 4.1 |
| 4 | Na-type ZSM-5 (3) | N-AEP | Beginning | 355 | 99.1 | 49.8 | 20.5 |
|  |  |  | After 32 days | 370 | 97.0 | 46.3 | 21.0 |
| Comp. Ex. 1 | H-type ZSM-5 (1) | N-AEP | Beginning | 355 | 100.0 | 51.4 | 15.1 |
|  |  |  | After 30 days | 370 | 76.7 | 33.6 | 17.9 |
| 2 | Na-type ZSM-5 (4) | N-AEP | Beginning | 380 | 97.9 | 24.2 | 28.5 |
|  |  |  | After 10 days | 400 | 81.8 | 19.7 | 30.6 |
| 3 | Na-type ZSM-5 (5) | N-AEP | Beginning | 365 | 99.3 | 38.1 | 16.8 |
|  |  |  | After 10 days | 380 | 82.1 | 32.4 | 18.2 |
| 4 | Na-type ZSM-5 (6) | N-AEP | Beginning | 355 | 99.3 | 49.7 | 18.9 |
|  |  |  | After 10 days | 380 | 91.9 | 39.9 | 19.4 |

According to the present invention, triethylenediamines and piperazines which are industrially useful, can be produced effectively and efficiently. Effects of the present invention are described below.

(1) According to the present invention, various amine compounds can be used as a material, and accordingly, the present invention can be used widely.

(2) The triethylenediamines and piperazines can be produced efficiently from various amine compounds by one step catalytic reaction.

(3) With the catalyst of the present invention, triethylenediamines and piperazines can be obtained with high yield. Further, said catalyst has a long life, and is useful as an industrial catalyst. Further, said catalyst can be prepared industrially, and a large amount of it can be produced stably at a low cost.

(4) The catalyst of the present invention has substantially no deterioration through the reaction, it can be activated easily by calcination operation, and it is thereby highly valuable as an industrial catalyst.

As mentioned above, the present invention has many and great characteristics, and provides all essentialities which have been desired, and accordingly, the present invention is highly useful.

What is claimed is:

1. A method for producing triethylenediamine or piperazine, which comprises contacting an amine compound selected from the group consisting of monoethanolamine, diethanolamine, N-(2-aminoethyl)ethanolamine, N-(2-hydroxyethyl)piperazine, N,N'-bis(2-hydroxyethyl)piperazine, N-(2-aminoethyl)piperazine, N,N'-bis(2- aminoethyl)piperazine, piperazine, ethylenediamine, diethylenetriamine, triethylenetetramine, and tetraethylenepentamine with a catalyst consisting of a crystalline aluminosilicate calcinated at a temperature of from 500 to 950° C. and then contacted with an inorganic acid, and having a molar ratio of silica to alumina of at least 12.

2. The method according to claim 1, wherein the crystalline aluminosilicate is a pentasyl type aluminosilicate.

3. The method according to claim 1, wherein the crystalline aluminosilicate has a molar ratio of silica to alumina of from 40 to 5,000.

4. The method according to claim 1, wherein the inorganic acid is at least one member selected from the group consisting of hydrogen chloride, hydrogen bromide, sulfuric acid, nitric acid and perchloric acid.

5. The method according to claim 4, wherein the inorganic acid is hydrogen chloride.

* * * * *